United States Patent
Saitou et al.

(10) Patent No.: US 9,594,050 B2
(45) Date of Patent: *Mar. 14, 2017

(54) A/F SENSOR ELEMENT AND METHOD OF MANUFACTURING THE SAME

(71) Applicant: DENSO CORPORATION, Kariya, Aichi-pref. (JP)

(72) Inventors: Masami Saitou, Nagoya (JP); Namitsugu Fujii, Yokkaichi (JP); Norikazu Kajiyama, Chiryu (JP)

(73) Assignee: DENSO CORPORATION, Kariya (JP)

(*) Notice: Subject to any disclaimer, the term of this patent is extended or adjusted under 35 U.S.C. 154(b) by 260 days.

This patent is subject to a terminal disclaimer.

(21) Appl. No.: 14/250,945

(22) Filed: Apr. 11, 2014

(65) Prior Publication Data

US 2014/0305798 A1 Oct. 16, 2014

(30) Foreign Application Priority Data

Apr. 12, 2013 (JP) .................. 2013-083492

(51) Int. Cl.
  *H01G 9/00* (2006.01)
  *G01N 27/407* (2006.01)
  *G01N 27/406* (2006.01)

(52) U.S. Cl.
  CPC ..... *G01N 27/4072* (2013.01); *G01N 27/4067* (2013.01); *G01N 27/4073* (2013.01)

(58) Field of Classification Search
  CPC ..................................... H01G 9/00
  See application file for complete search history.

(56) References Cited

U.S. PATENT DOCUMENTS

| 4,908,119 A | 3/1990 | Saito et al. |
| 5,935,399 A | 8/1999 | Tanaka et al. |
| 5,956,841 A | 9/1999 | Watanabe et al. |
| 6,354,134 B1 | 3/2002 | Katafuchi et al. |
| 6,527,928 B1 | 3/2003 | Watanabe et al. |

(Continued)

FOREIGN PATENT DOCUMENTS

| JP | 53-34756 | 9/1978 |
| JP | 53-139595 | 12/1978 |

(Continued)

OTHER PUBLICATIONS

Japanese Office Action (2 pages) dated Apr. 14, 2015, issued in corresponding Japanese Patent Application No. 2013-083492 and English translation (3 pages).

*Primary Examiner* — Seahvosh Nikmanesh
(74) *Attorney, Agent, or Firm* — Nixon & Vanderhye PC

(57) ABSTRACT

An A/F sensor element includes a substrate made of an insulating ceramic having a bottomed cylindrical shape, an electrolyte part made of a solid electrolyte, and a pair of electrode portions. The electrolyte part is embedded in at least a portion of the side wall of the substrate. The A/F sensor element is used by inserting a rod-like heater in the substrate having the bottomed cylindrical shape. The substrate is formed of the insulating ceramic at a contact position to the heater within the substrate. In a manufacturing of the substrate, a molded body having a space for a forming position of the electrolyte part is formed by using substrate-forming clay, and then the molded body is molded by filling electrolyte-forming clay into the space.

3 Claims, 13 Drawing Sheets

(56) References Cited

U.S. PATENT DOCUMENTS

| | | | |
|---|---|---|---|
| 2003/0101569 A1 | 6/2003 | Watanabe et al. | |
| 2013/0240354 A1 | 9/2013 | Saitou et al. | |
| 2014/0305797 A1* | 10/2014 | Saitou | B29C 45/0001 |
| | | | 204/408 |

FOREIGN PATENT DOCUMENTS

| | | |
|---|---|---|
| JP | 54-118293 | 9/1979 |
| JP | 7-198673 | 8/1985 |
| JP | 61-272649 | 12/1986 |
| JP | 63-61160 | 3/1988 |
| JP | 3-138559 | 6/1991 |
| JP | 04-49003 | 2/1992 |
| JP | 09-203718 | 8/1997 |
| JP | 9-304337 | 11/1997 |
| JP | 11-153571 | 6/1999 |
| JP | 11-183430 | 7/1999 |
| JP | 2007-218741 | 8/2007 |
| JP | 2007-278941 | 10/2007 |
| JP | 2010-145214 | 7/2010 |
| JP | 2011-17560 | 1/2011 |
| JP | 2013-195140 | 9/2013 |

* cited by examiner

A/F SENSOR ELEMENT AND METHOD OF MANUFACTURING THE SAME

CROSS-REFERENCE TO RELATED APPLICATION

This application is based on and claims the benefit of priority from earlier Japanese Patent Application No. 2013-83492 filed Apr. 12, 2013, the description of which is incorporated herein by reference.

TECHNICAL FIELD

The present disclosure relates to a bottomed cylindrical shaped A/F sensor element used by inserting a heater therein, and relates to a method of manufacturing the same.

BACKGROUND

An A/F sensor for vehicle is used for detecting a combustion condition in an internal combustion engine by detecting an oxygen concentration in a measurement gas (exhaust gas).

As an example for automobiles, an A/F sensor is a product that detects an oxygen concentration in a measurement gas (exhaust gas) using an electromotive force as limit current generated in a solid electrolyte of the A/F sensor element due to an oxygen concentration difference between a reference gas and the measurement gas (exhaust gas) as an output.

An oxygen sensor element of one cell type is widely used for the A/F sensor element.

Generally, the A/F sensor element is composed of a solid electrolyte such as zirconium oxide partially stabilized with yttria, and a pair of platinum electrodes provided on both surfaces of the solid electrolyte.

A surface which is exposed to the exhaust gas of the electrode among the pair of electrodes of the A/F sensor element is provided with a diffusion resistance layer made of a porous ceramic.

The diffusion resistance layer can allow the measurement gas such as the exhaust gas to permeate therethrough, thus the measurement gas is introduced into the element via through holes of the diffusion resistance layer, and reaches the electrode formed on the solid electrolyte.

Since it is necessary to partition spatially the exhaust gas and atmosphere, which is a reference oxygen concentration, by the solid electrolyte in the A/F sensor element, an A/F sensor element having a bottomed cylindrical shape or a plate shape is used.

Since the plate-shaped A/F sensor element plate can be manufactured by laminating sheets of solid electrolyte layers or insulating layers, it is easy to manufacture.

Further, since it becomes possible to laminate-form a heater integrally with the solid electrolyte layers for heating the element, it is easy to heat the solid electrolyte layer.

However, due to its plate-like overall shape, corners are formed at ends, and the element is poor at handling thermal shock in a usage environment or when being covered by water in an exhaust pipe, so that there is a possibility that the element may be damaged.

On the other hand, since a bottom can be formed in a curved surface in the bottomed-cylindrical-shaped A/F sensor element, thermal shock is dispersed, thus it is advantageous that cracks due to the water or the like can be prevent from occurring.

An element made entirely of a solid electrolyte such as zirconia device as the A/F sensor element having the bottomed cylindrical shape has been developed, for example (refer to Japanese Patent Application Laid-Open Publication No. 53-139595).

However, zirconia has low thermal conductivity.

Therefore, if a whole A/F sensor element is formed by zirconia, the time it takes to heat the element sufficiently becomes longer when heating the element by a heater inserted and disposed in the element having the bottomed cylindrical shape.

As a result, there is a problem that a quick activation of the A/F sensor element cannot be performed.

Further, partially stabilized zirconia in which expensive rare earths such as yttria is added to zirconia is used as the solid electrolyte in recent years.

However, an amount of rare earth increases if entire element is formed by the solid electrolyte made of partially stabilized zirconia as in the conventional art, manufacturing cost increases.

SUMMARY

An embodiment provides an A/F sensor element that can be manufactured at low cost and capable of quick activation, and a method of manufacturing the same.

In an A/F sensor element according to a first aspect, the A/F sensor element includes a substrate made of an insulating ceramic having a bottomed cylindrical shape with a closed distal end and an opened rear end, an electrolyte part made of a solid electrolyte, and a pair of electrodes.

The insulating ceramics is made of a material having a higher thermal conductivity than the solid electrolyte, the electrolyte part is embedded in at least a portion of the side wall of the substrate to constitute a part of the sidewall, and the pair of the electrode portion is formed on an inner surface and an outer surface of the side wall, respectively, and is formed at positions sandwiching the electrolyte part.

The A/F sensor element is used by inserting a rod-like heater in the substrate having the bottomed cylindrical shape, and the substrate is formed of the insulating ceramic at a contact position to the heater within the substrate.

According to the A/F sensor element mentioned above, the electrolyte part made of the solid electrolyte is embedded in at least the portion of the side wall of the substrate made of the insulating ceramic to constitute the part of the side wall.

Therefore, it becomes possible to reduce the amount of the solid electrolyte to be used. As a result, even if the partially stabilized zirconia to which the expensive rare earths such as yttria is added to the zirconia as the solid electrolyte, for example, the amount to be used can be reduced.

Therefore, the A/F sensor element can be manufactured at low cost.

Further, by constituting the part of the side wall with the electrolyte, it becomes possible to reduce the size of the A/F sensor element.

Thereby, it becomes possible to quickly heat the A/F sensor element, thus the quick activation is improved.

Further, the A/F sensor element is used by inserting a rod-like heater in the substrate that has the bottomed cylindrical shape, and the substrate is made of an insulating ceramic having a higher thermal conductivity than the solid electrolyte at the contact position to the heater within the substrate.

That is, the electrolyte part made of the solid electrolyte having a low thermal conductivity is not present in the contact position to the heater in the substrate, but the insulating ceramic with the high thermal conductivity is present.

Therefore, heat from the heater is transmitted immediately to the substrate made of the insulating ceramic having the high thermal conductivity.

Therefore, it becomes possible that the time required for heating is shortened, thus the A/F sensor element can be activated quicker.

Further, the A/F sensor element has the substrate having the bottomed cylindrical shape.

Therefore, it becomes possible to avoid formation of corners or level differences where thermal stress is easily concentrated when covered by water, like a laminated plate-like A/F sensor element, for example.

Therefore, it becomes possible to further avoid the occurrence of cracks due to stress concentration.

Further, it becomes possible to avoid the formation of the corners as described above, it becomes possible to prevent the element from being damaged by the collision of the corners when being assembled to another member. Therefore, assembling to the other member becomes easy.

In the A/F sensor element according to a second aspect, wherein, the part of the side wall of the substrate is made of the electrolyte part, and the distal end side and the rear end side from the electrolyte part of the side wall is formed by the insulating ceramic.

In the A/F sensor element according to a third aspect, wherein, a level difference at a boundary section between the substrate and the electrolyte part is 30 μm or less.

In the A/F sensor element according to a fourth aspect, the substrate has the bottomed cylindrical shape.

In the A/F sensor element according to a fifth aspect, the insulating ceramic is alumina.

In the A/F sensor element according to a sixth aspect, the solid electrolyte is a partially stabilized zirconia.

In the A/F sensor element according to a seventh aspect, the electrolyte part is formed in a size of ½ or less of the volume of the substrate.

In the A/F sensor element according to an eighth aspect, there is provided a diffusion resistance layer made of a porous ceramic that covers at least the electrode portion formed on an outer surface of the substrate.

In a method of manufacturing the A/F sensor element according to a ninth aspect, the method includes a first molding step for molding substrate-forming clay containing the insulating ceramic material to the shape of the substrate to which a space is formed in a position where the electrolyte part is formed, a second molding step for molding electrolyte-forming clay containing a solid electrolyte material by being filled in the space, a firing step for manufacturing the substrate having the electrolyte part by firing, and an electrode molding step for forming the electrode portion.

The A/F sensor element may be manufactured by performing the first molding step, the second molding step, the firing step, and the electrode molding step.

In the first molding step, substrate-forming clay containing the insulating ceramic material is molded to the shape of the substrate to which a space is formed in a position where the electrolyte part is formed.

In the first molding step, it is possible to appropriately adjust the size of the space for forming the electrolyte part, and the size of the space can be reduced as required.

Therefore, it is possible to reduce the amount of the electrolyte-forming clay filled in the second molding step performed after the first molding step.

As a result, it becomes possible to reduce the manufacturing cost of the A/F sensor element.

Further, by adjusting the formation position of the space, it is possible to control the formation position of the electrolyte part in the first molding step.

Then, it is possible to form the space for the formation position of the electrolyte part in the portion of the side wall of the substrate having the bottomed cylindrical shape.

Accordingly, the contact position to the heater can be adjusted so that the contact position can be formed by the insulating ceramic.

As a result, the A/F sensor element that can activate quickly can be manufactured.

By performing the first molding step and the second molding step, the substrate-forming clay and the electrolyte-forming clay can be molded integrally into the bottomed cylindrical shape.

As a result, by performing the firing step, the substrate of the bottomed cylindrical shape having the electrolyte part made of a solid electrolyte embedded in at least the part of the side wall can be obtained.

In the second molding step, the electrolyte-forming clay is filled into the space formed in advance in the first molding step, and is integrally formed as described above, therefore, it becomes possible to almost eliminate the level difference at the boundary section between the substrate and the electrode after firing.

Therefore, it becomes possible to suppress the occurrence of the stress concentration on the level difference between the substrate and the electrode during the thermal shock such as the A/F sensor element in the firing or being covered by water, and it becomes possible to manufacture the A/F sensor element that prevents cracks from occurring.

In the method of manufacturing the A/F sensor element according to a tenth aspect, the electrolyte-forming clay and the substrate-forming clay are molded by injection using a metal mold in the first molding step and the second molding step.

In the method of manufacturing the A/F sensor element according to an eleventh aspect, the substrate-forming clay is molded by injection into a cavity of the mold in a state where a forming position of the electrolyte part in the cavity of the mold is closed by a movable mold in the first molding step, and the electrolyte-forming clay is molded by injection into the space formed by opening the forming position of the electrolyte part closed by the movable mold in the second molding step.

DETAILED DESCRIPTION OF THE PREFERABLE EMBODIMENTS

Figure 1:
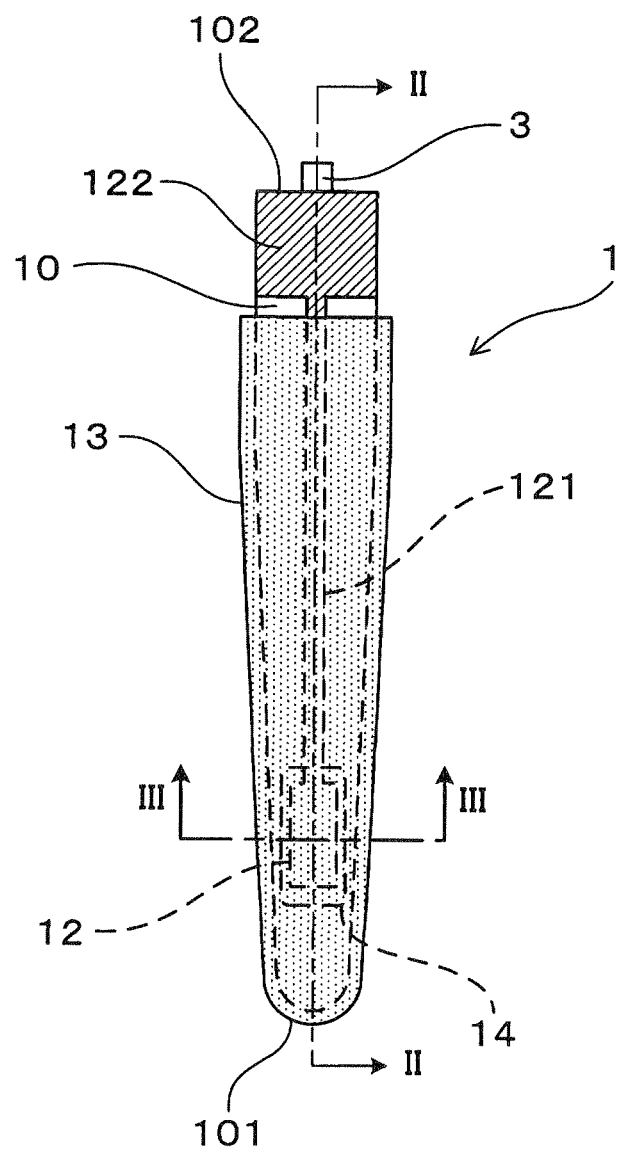
FIG. 1 shows a side view of a A/F sensor element in a first embodiment.

A preferable embodiment of an A/F sensor element will be described hereinafter.

In the A/F sensor element, a substrate has a bottomed tubular hollow shape with a closed distal end and an opened rear end, and the A/F sensor element is referred to a so-called cup-shaped, cylindrical, or filled distal shape type.

In the present specification, an end to be inserted into an exhaust manifold and/or an exhaust pipe of an internal combustion engine is referred to as a distal end, and an opposite end that is exposed from the exhaust manifold and/or the exhaust pipe is referred to as a rear end.

The A/F sensor element can detect the oxygen concentration in the exhaust gas by detecting the limit current between the solid electrolytes of the elements from the difference of oxygen concentration between the reference gas and the exhaust gas.

Thus, the A/F sensor element is able to detect the air-fuel ratio (A/F).

The A/F sensor element has a bottomed cylindrical molded body made of an insulating ceramic, and an electrolyte part made of a solid electrolyte formed integrally with the substrate.

The electrolyte part is embedded in at least a part of a side wall of the bottomed cylindrical shaped substrate and forms a part of the side wall.

The electrolyte part may be formed integrally with the substrate by co-firing.

In the A/F sensor element, the electrolyte part is formed by a portion of or a plurality of portions of the side wall of the substrate is replaced with the solid electrolyte.

The A/F sensor element is used by inserting a rod-like heater (heater rod) in the substrate.

It becomes possible to reduce the time it takes an oxygen ion conductivity of the solid electrolyte to occur by heating the A/F sensor element with the heater inserted and disposed in the substrate.

The substrate is made of insulating ceramics, as described above, at a contact position to the heater within the substrate.

When the electrolyte part made of the solid electrolyte is formed at the contact position, the heat from the heater is transmitted to the substrate through the electrolyte part having a low thermal conductivity, thus the time required to raise the temperature of the A/F sensor element to a predetermined temperature needed to function as a sensor becomes long.

In other words, a quick activation of the A/F sensor element is difficult.

In the A/F sensor element, the contact position to the heater within the substrate can be adjusted by adjusting an outer diameter of the rod-like (cylindrical) heater or an inner diameter of the substrate, or forming an incline to the side wall of the substrate so that the inner diameter thereof becomes smaller toward the distal end.

Preferably, the contact position of the substrate to the heater may be at a distal-end-sided position than the electrolyte part.

More specifically, the contact position is preferably at the side wall or a bottom portion of the substrate in the distal-end-sided position than the electrolyte part.

More preferably, the heater is inserted so that one end in an axial direction of the rod-like heater contacts the bottom portion of the substrate, for example.

Preferably, a part of the side wall of the substrate is made of the electrolyte part, and a distal end side and a rear end side of the electrolyte part of the substrate are made of the insulating ceramics.

In this case, it becomes possible to easily achieve the above configuration that the contact position of the substrate to the heater is the insulating ceramics with high thermal conductivity by insert-disposing the rod-like heater in the substrate, and having the one end of the heater contacting the bottom portion of the substrate, or contacting with the side wall in the distal-end-sided position than the electrolyte part, for example.

Further, since it becomes possible to reduce the size of the electrolyte part made of an expensive solid electrolyte in this case, it becomes possible to reduce the manufacturing cost of the A/F sensor element.

Further, it is preferable that a level difference at a boundary section between the substrate and the electrolyte part is 30 μm or less in the A/F sensor element.

In this case, a stress concentration generated during a thermal shock may be reduced in the level difference, therefore cracks are prevented from occurring.

In order to avoid further cracking, the level difference at the boundary section is preferably 10 μm or less, and more preferably, 5 μm or less.

If a corner, such as a part that protrudes from surroundings or a sharp edge, or a level difference is present on an outer surface of the substrate in the A/F sensor elements, there is a possibility that stress concentration occurs in the corner or the level difference during thermal shock, and may cause cracks.

In order to prevent the cracks from occurring, the substrate is preferably formed in a bottomed cylindrical shape.

From the same viewpoint, the boundary between the sidewall and the bottom portion is preferably formed in the curved surface in the substrate having the bottomed cylindrical shape.

The substrate may be composed of various insulating ceramics.

The insulating ceramic may employ a single or a mixture of two or more materials selected from materials such as alumina, zirconia, yttria, magnesia, calcia, silica and the like, for example.

Preferably, the insulating ceramic is alumina.

In this case, it becomes possible to improve a thermal conductivity and an electrical insulation of the substrate.

It should be noted that alumina means a material whose main component is aluminum oxide ($Al_2O_3$).

A content of aluminum oxide in the insulating ceramics is preferably 90 wt % or more.

In addition to alumina, the insulating ceramics may contain a single or a mixture of two or more materials selected from materials such as zirconia, yttria, magnesia, calcia, silica and the like, for example.

Further, the solid electrolyte is preferably a partially stabilized zirconia.

In this case, it becomes possible to improve a detection sensitivity of the A/F sensor element.

The partially stabilized zirconia is composed of zirconia (zirconium dioxide, $ZrO_2$) as a main component, and 4-8 mol % of yttria ($Y_2O_3$) relative to zirconia, for example, is added.

Further, in addition to yttria and zirconia, the partially stabilized zirconia may contain a single or a mixture of two or more materials selected from materials such as alumina, magnesia, calcia, silica and the like.

Further, in the A/F sensor element, the electrolyte part is preferably formed in a size of ½ or less of the volume of the substrate.

In this case, since it becomes possible to reliably reduce the size of the electrolyte part made of relatively expensive solid electrolyte, it becomes possible to reduce the manufacturing cost of the A/F sensor element.

Further, in this case, since it becomes possible to reduce the size of the electrolyte part made of the solid electrolyte having a low thermal conductivity as compared with the insulating ceramics, it becomes easy to warm up the A/F sensor element during heating, and a quick activation of the A/F sensor element can be further improved.

From the same viewpoint, the electrolyte part is preferably formed in a size of ⅕ or less of the volume of the substrate, and more preferably, in a size of 1/10 or less.

Further, if an inner diameter of the substrate is too small, it becomes difficult to ensure a sufficient amount of the reference gas necessary for the measurement in the substrate, and there is a possibility that the sensor characteristic is deteriorated.

On the other hand, if the inner diameter of the substrate is too large, the size of the A/F sensor element increases, and there is a possibility that the time it takes to activate the element upon heating increases.

From the viewpoints of these, the inner diameter of the substrate is preferably 1-10 mm, and more preferably, 1-4 mm.

It is also possible to employ a substrate whose inner diameter changes by forming an inclined to a side wall of the substrate.

Specifically, the incline may be formed to the side wall so that the inner diameter of the substrate becomes smaller toward the distal end from the rear end.

In this case, it is preferable that at least an inner diameter of an opening of the substrate is within the above range.

Further, the A/F sensor element may be provided with an element cover for covering an outer surface thereof.

The strength of the A/F sensor element can be reinforced by the element cover, however, when the thickness of the substrate is too small, the strength of the A/F sensor element becomes weak, and there is a possibility that the element becomes fragile.

Thus, the thickness of the substrate is preferably at least 0.1 mm or more, and more preferably, 0.3 mm or more.

On the other hand, if the thickness of the substrate is too thick, there is a possibility that the time it takes to activate the element upon heating increases.

Thus, the thickness of the element is preferably 5 mm or less, and 3 mm or less even more preferably.

Further, the A/F sensor element has a pair of electrode portions formed on inner and outer surfaces of the side wall, respectively.

The pair of the electrode portions is formed at positions sandwiching the electrolyte part that is embedded in the side wall of the substrate.

For example, a measured gas side electrode may be formed on the outer surface of the substrate, and a reference gas side electrode may be formed on the inner surface of the substrate.

The pair of electrode portions may be formed by a noble metal such as platinum. Preferably, the electrode portion is formed of platinum.

Further, when the thickness of the electrode portion is too thick, particularly in the electrode portion that serves as the measured gas side electrode, a part where three components of the electrolyte part (solid electrolyte), the electrode portion (noble metal), and the exhaust gas overlap is reduced, thus there is a possibility that the sensor characteristic is deteriorated.

Therefore, the thickness of the electrode portion is preferably 5 μm or less, and more preferably, 3 μm or less.

On the other hand, when the thickness of the electrode portion is too small, and if the electrode is made of a metal component such as Pt, a gap of the metal component increases, thus there is a possibility that the conductivity of the electrode portion deteriorates.

Thus, the thickness of the electrode portion is preferably 0.3 μm or more.

Further, the electrode portion is preferably a plating electrode.

In this case, it becomes possible to form an electrode portion having a high electrical conductivity, and particularly in the electrode portion that serves as the measured gas side electrode, there is a tendency of easily increasing the part where three components of the electrolyte part, the electrode portion, and the exhaust gas overlap.

In contrast, the electrode portion formed by printing a conductive paste material or sputtering, for example, a particle growth of the conductive metal components occurs during baking, thus there is a possibility that the metal component is aggregated in an island-like shape.

Therefore, in order to avoid the particle growth, it is necessary to further add other metal or ceramic particles into the electrode material other than the conductive metal particles such as Pt.

As a result, the thickness of the electrode portion required to obtain the conductivity becomes inevitably thick, and there is a tendency that reactivity in the electrode portion is reduced.

Further, the electrode portion (measured gas side electrode) having the same size as the electrolyte part may be formed on the electrolyte part, for example, on the outer surface of the substrate.

Moreover, an electrode lead portion extending to the rear end side of the substrate from the measured gas side electrode may be formed on the outer surface of the substrate.

The electrode lead portion is electrically connected to the measured gas side electrode formed on the electrolyte part, and is for outputting an electrochemical cell formed by the electrolyte part and the electrode portion.

The electrode lead portion may be formed by, for example, noble metal similar to the electrode portion.

Further, the electrode lead part is preferably disposed so as not to be formed on the electrolyte part.

In other words, it is preferable that the electrolyte part on the outer surface of the substrate is completely covered by the electrode portion (measured gas side electrode).

In this case, it becomes possible to improve the detection accuracy of the A/F sensor element.

If the electrode lead portion is formed on the electrolyte part, an oxygen ion conductive reaction occurs also on the electrode lead part, thus there is a possibility that the detection accuracy as the A/F sensor decreases.

On the other hand, the electrode portion (reference gas side electrode) that covers at least the electrolyte part may be formed on the inner surface of the substrate.

The reference gas side electrode may also be formed on the entire inner surface of the substrate.

A formation area of the electrode portion (measured gas side electrode) on the outer surface of the substrate is preferably ⅕ or less of an area of the outer surface of the substrate.

In this case, it becomes possible to reduce a formation region of a diffusion resistance layer or a protective layer when forming the diffusion resistance layer or the protective layer that covers the electrode portion as described below, thereby improving the productivity of the A/F sensor element.

Further, when forming the diffusion resistance layer or the protective layer by thermal spraying, the time it takes to spray reduces as the processing area decreases, thereby improving the productivity greatly.

Further, to reducing the formation region of the diffusion resistance layer or the protective layer leads to reduce the size of the A/F sensor element.

As a result, it becomes possible to further improve the quick activation of the elements during heating.

Further, the A/F sensor element is preferred to have the diffusion resistance layer made of a porous ceramic that covers at least the electrode portion formed on an outer surface of the substrate.

In this case, it is possible to suppress the diffusion of gas to the surface of the electrode portion (measured gas side electrode) formed on the outer surface of the substrate.

Therefore, it is possible to increase the detection accuracy of the sensor.

The diffusion resistance layer may be composed of a porous body of refractory metal oxides such as $MgO.Al_2O_3$ spinel.

If the thickness of the diffusion resistance layer is too thin, it is impossible to obtain a sufficient limit current, therefore, there is a possibility that the detection performance of the sensor decreases.

If the thickness is too thick, the body size of the element is increased and may adversely affect the quick activation of the element.

Therefore, the thickness of the diffusion resistance layer is preferably equal to or more than 50 μm and 500 μm or less, and more preferably, equal to or more than 50 μm and 300 μm or less.

Further, the protective layer that covers at least a portion of the diffusion resistance layer may be formed in the A/F sensor element.

The protective layer may be formed by the ceramics such as $MgO.Al_2O_3$ spinel having excellent heat resistance similarly to in the diffusion resistance.

The protective layer may be either porous or dense body material.

When using the protective layer made of porous body material, it is possible to form a protective layer to cover a whole diffusion resistance layer.

In addition to the diffusion resistance layer, the protective layer made of porous material can be formed to cover a whole outer surface of the substrate, or from the distal end to at least an area that is inserted into the exhaust gas pipe or the exhaust manifold.

Further, when using the protective layer made of dense body material, it is preferred that at least a portion of the diffusion resistance layer exposes on the outer surface of the A/F sensor element so that a region where the diffusion resistance layer is not covered by the protective layer is formed.

Moreover, the protection of the electrodes becomes insufficient if the thickness of the protective layer is too thin, and the body size element is increased if the thickness is too thick, and may adversely affect the quick activation of the element.

Therefore, the thickness of the protective layer is preferably equal to or more than 50 μm and 500 μm or less, and more preferably, equal to or more than 50 μm and 300 μm or less.

The diffusion resistance layer and the protective layer may be formed by, for example, blowing ceramic powder of $MgO.Al_2O_3$ spinel or the like by spraying.

The A/F sensor element may be manufactured by performing a first molding step, a second molding step, a firing step, and an electrode molding step.

In the first molding step, substrate-forming clay containing the insulating ceramic material is molded to the shape of the substrate to which a space is formed in a position where the electrolyte part is formed.

Alumina powder, for example, may be used as the insulating ceramic material.

Alumina may be used as a main component of the insulating ceramic material, and a single or a mixture of two or more materials selected from materials such as zirconia, yttria, magnesia, calcia, silica and the like, for example may be further used.

The substrate-forming clay may be obtained by mixing the insulating ceramic material, organic binder, dispersant, water and the like.

In the second molding step, electrolyte-forming clay containing a solid electrolyte material is molded by being filled in the space mentioned above.

A raw material that produces a solid electrolyte after firing may be used as the solid electrolyte material.

Specifically, zirconia powder, yttria powder or the like may be used as the solid electrolyte material.

Other than that, a material that contains a single or a mixture of two or more materials selected from materials such as alumina powder, silica powder, powder magnesia powder, calcia powder and the like may be used as the solid electrolyte material.

The electrolyte-forming clay may be obtained by mixing the solid electrolyte material, the organic binder, the dispersant, water and the like.

The first molding step and the second molding step may be performed by an injection molding method using a metal mold, or by a cast molding method using a plaster/resin mold.

Preferably, the respective electrolyte-forming clay and the substrate-forming clay are molded by injection using the metal mold in the first molding step and the second molding step.

In this case, the A/F sensor element with a small level difference in the boundary between the substrate and the electrolyte part can be easily produced.

Preferably, the substrate-forming clay is molded by injection into a cavity of the mold in a state where the forming position of the electrolyte part in the cavity of the mold is closed by a movable mold in the first molding step, and the electrolyte-forming clay is molded by injection into the space formed by opening the forming position of the electrolyte part closed by the movable mold in the second molding step.

In this case, the substrate made of the insulating ceramic having the bottomed cylindrical shape in which one end is closed and another end is opened, and the electrolyte part being embedded in at least a portion of the side wall of the substrate to constitute a part of the side wall can be formed easily.

In the firing step, a molded body obtained by performing the first molding step and the second molding step is fired.

The firing temperature may be appropriately determined depending on the composition of the insulating ceramic and the solid electrolyte.

In addition, it is preferred that a degreasing step that degreases the molded body be performed before performing the firing step.

The organic components such as the binder contained in the molded body can be removed before firing by performing the degreasing step.

In the electrode molding step, a pair of the electrode portions is formed onto the inner surface and the outer surface of the substrate, respectively.

The pair of the electrode portions is formed at positions sandwiching at least the electrolyte part in the side wall of the substrate.

In the electrode molding step, it is preferable to form the electrode portion by plating.

The heating temperature for forming the electrode portion is preferably 1200 degrees C. or less.

EMBODIMENT

First Embodiment

Hereinafter will be described an embodiment of an A/F sensor element.

As shown in FIG. 1-FIG. 4, an A/F sensor element 1 of the present embodiment has a substrate 10 made of an insulating ceramic having a bottomed cylindrical shape in which a distal end 101 is closed and a rear end 102 is opened, an electrolyte part 103 made of a solid electrolyte, and a pair of electrode portions 11, 12.

Figure 2:
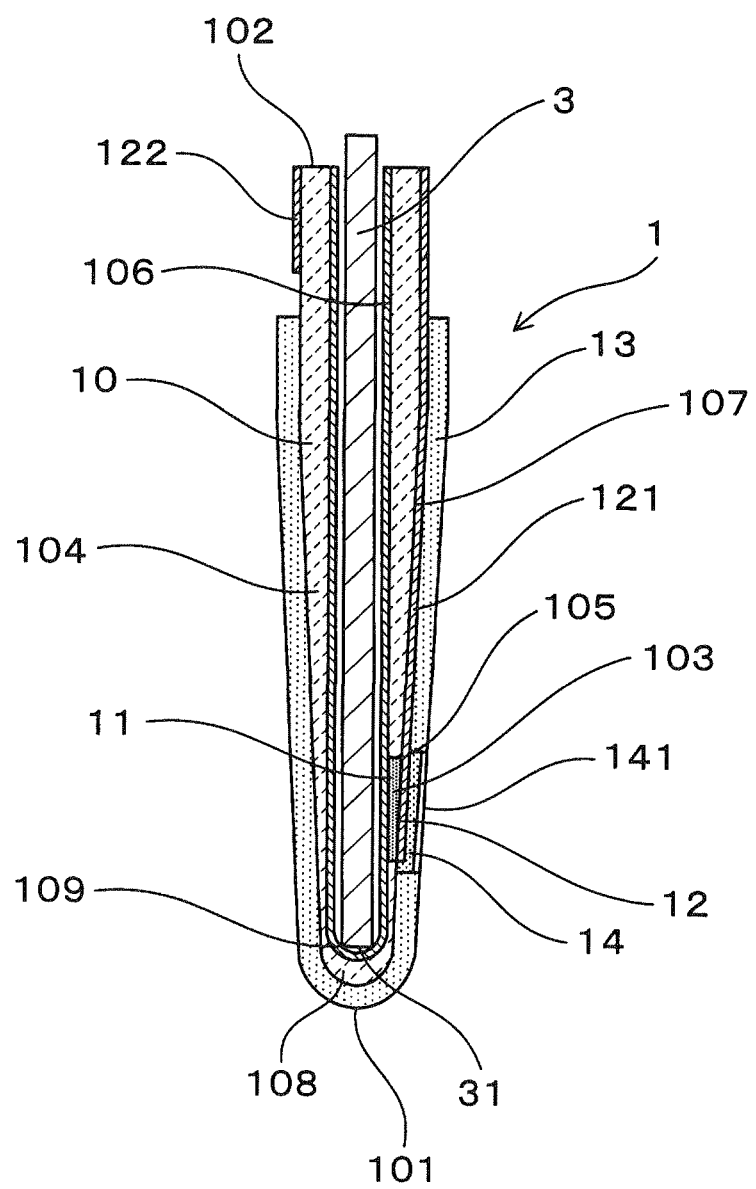
FIG. 2 shows a sectional view taken along a line II-II in FIG. 1.
Figure 3:
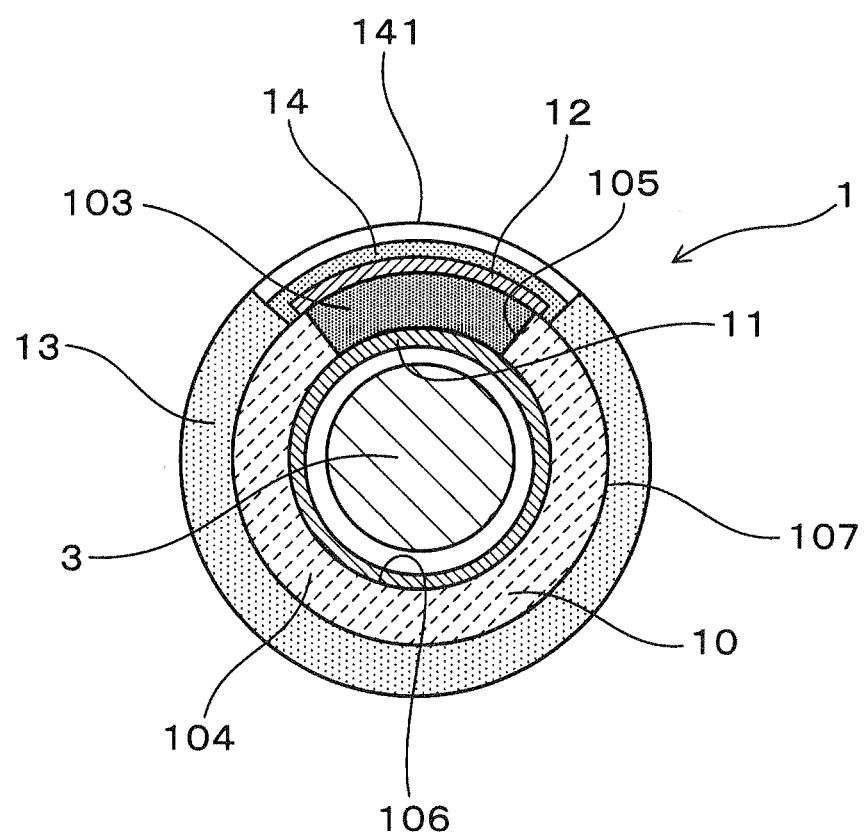
FIG. 3 shows a sectional view taken along a line III-III in FIG. 1.
Figure 4:
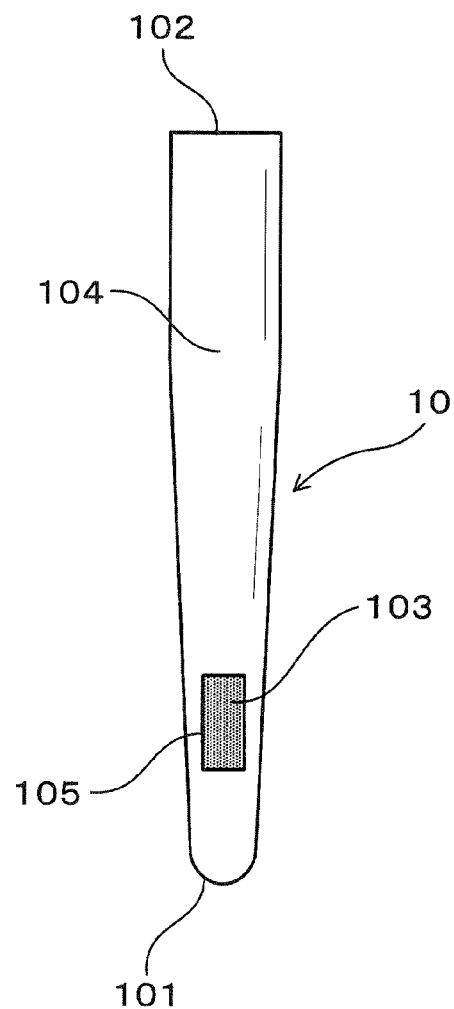
FIG. 4 shows a side view of a substrate of which an electrolyte part is formed in a part of a side wall in the first embodiment.

The electrolyte part 103 is embedded in at least a portion of a side wall 104 of the substrate 10 to constitute a part of the side wall 104 of the substrate 10 (refer to FIG. 2-FIG. 4).

The pair of electrode portions 11, 12 is formed on an inner surface 106 and an outer surface 107 of the side wall 104, respectively, and is formed at positions sandwiching the electrolyte part 103.

In FIG. 1, for convenience of explanation, an outer shape of the body 10, the electrode portion 12 formed on the outer surface 107, an electrode lead 121 portion which will be explained later, and the diffusion resistance layer 14 are indicated by dotted lines, while an electrode extraction portion 122 which will be explained later, a part of the electrode lead 121 portion, and the protective layer 13 are indicated by shading with points or hatchings.

Hereinafter, the A/F sensor element 1 of the present embodiment will be described in detail with reference to FIG. 1-FIG. 4.

As shown in FIG. 1-FIG. 4, the A/F sensor element 1 of the present embodiment has the substrate 10 made of the insulating ceramic having the bottomed cylindrical shape.

As shown in FIG. 2, a boundary between the side wall 104 and a bottom portion 108 of the substrate 10 has a curved surface, and a whole bottom surface is a curved surface. The substrate 10 has a uniform thickness of 1 mm.

As shown in FIG. 2-FIG. 4, the substrate 10 has a structure that a part of the side wall 104 is replaced by a solid electrolyte, and the electrolyte part 103 made of the solid electrolyte is formed on the side wall 104 of the substrate 10.

That is, in the A/F sensor element 1, the electrolyte part 103 made of the solid electrolyte is embedded in at least a portion of the side wall 104 of the substrate 10 made of the insulating ceramic to constitute a part of the side wall 104 of the substrate 10.

The electrolyte part 103 is formed on an end of the closed side of the side wall 104 of the substrate 10, i.e., closer to the distal end 101.

A part of the side wall 104 of the substrate 10 is formed by the electrolyte part 103 made of the solid electrolyte, and the distal end 101 side and the rear end 102 side of the electrolyte part 103 of the substrate 10 are all made of the insulating ceramics.

The electrolyte part 103 is sufficiently small relative to the substrate 10, and the electrolyte part 103 is formed in a size of 1/30 of a total volume of the substrate 10.

There is almost no level difference at a boundary section 105 between the substrate 10 and the electrode 103, and in the present embodiment, even in any of the inner surface 106 and the outer surface 107 of the substrate 10, the level difference at the boundary section 105 between the substrate 10 and the electrode 103 is no more than 3 μm (refer to FIGS. 2-4).

In the present embodiment, the insulating ceramic is made of alumina having a thermal conductivity of 40 W/m·K. The solid electrolyte is made of partially stabilized zirconia having the thermal conductivity of 15 W/m·K. The partially stabilized zirconia has zirconia as a main component, and contains 4-8 mol % of yttria.

Further, as shown in FIG. 1-FIG. 3, the A/F sensor element 1 of the present embodiment is used by inserting a rod-like heater 3 in the substrate 10.

As shown in FIGS. 2 and 3, the substrate 10 is constituted of the insulating ceramic having a higher thermal conductivity than the solid electrolyte at a contact position 109 to the heater 3 within the substrate 10.

That is, the electrolyte part 103 made of the solid electrolyte having a low thermal conductivity is not present in the contact position 109 to the heater 3 the substrate, but the insulating ceramic with a high thermal conductivity is present.

In the present embodiment, an inner diameter of the rear end 102 of the substrate 10, i.e., the inner diameter of an opening end portion is 3 mm, and a diameter of the heater 3 inserted into the substrate 10 is 1.5 mm.

Then, when the heater 3 is inserted into the substrate 10, one end 31 in an axial direction of the heater 3 contacts the bottom portion 108 of the substrate, and the bottom portion 108 is composed of the insulating ceramic.

Further, as shown in FIG. 1-FIG. 3, the pair of the electrode portions 11, 12 sandwiching the electrolyte part 103 is formed on the inner surface 106 and the outer surface 107 of the substrate 10.

The pair of the electrode portions 11, 12 is made of platinum and formed in fpm thickness. The electrode portions 11, 12 are plating electrodes.

A reference gas side electrode 11 and a measured gas side electrode 12 are formed as the electrode portions 11, 12 in the present embodiment.

That is, the reference gas side electrode 11 is formed on the inner surface 106 of the substrate 10, and the measured gas side electrode 12 is formed on the outer surface 107 of the substrate 10.

In the A/F sensor element 1, an electrochemical cell is formed by the electrolyte part 103 and the pair of the electrode portions 11, 12 that sandwiches the electrolyte part 103.

In the present embodiment, the reference gas side electrode 11 is formed so as to cover the entire surface of the inner surface 106 of the substrate 10.

On the other hand, the measured gas side electrode 12 is formed in a region overlapping with the electrolyte part 103 on the outer surface 107 of the substrate 10.

Further, the electrode lead portion 121 extending toward the rear end 102 side of the substrate 10 from the measured gas side electrode 12 is formed the outer surface 107 of the substrate 10.

The electrode lead portion 121 is formed on the outer surface 107 of the substrate 10 made of the insulating ceramic, and is not formed on the electrolyte part 103 made of the solid electrolyte.

Further, the ring-shaped electrode extraction portion 122 that surrounds an outer periphery of the substrate 10 is formed in the rear end 102 side of the substrate 10, and the electrode extraction portion 122 is connected to the electrode lead portion 121 and electrically conducted.

Similarly to the electrode portions 11, 12, the electrode lead portions 121 and the electrode extraction portion 122 are made of platinum (Pt), and are formed with the same thickness as the electrode portion.

In the A/F sensor element 1 of the present embodiment, as shown in FIGS. 1 to 3, a diffusion resistance layer 14 made of a porous ceramic that covers the measured gas side electrode 12 is formed in order to suppress a diffusion of the measured gas (exhaust gas) on to a surface of the measured gas side electrode 12.

The diffusion resistance layer 14 is a layer of porous made of $MgO \cdot Al_2O_3$ spinel, and formed with a thickness of 200 μm (maximum thickness).

Further, a protective layer that covers the outer surface of the substrate 10 is formed thereto.

The protective layer 13 is made of a non-porous material (dense body) of $MgO \cdot Al_2O_3$ spinel with a thickness (maximum thickness) of 300 μm.

The protective layer 13 does not completely cover the diffusion resistance layer 14, and the diffusion resistance layer 14 is at least partially exposed on the outer surface of the A/F sensor element.

The protective layer 13 is hardly permeates the exhaust gas in the present embodiment.

Thus, the A/F sensor element 1 of the present embodiment is configured so that the exhaust gas reaches the measured gas side electrode 12 from a region where no protective layer 13 is formed on the diffusion resistance layer 14, i.e., from an opening 141 where the diffusion resistance layer 14 is exposed through the diffusion resistance layer 33.

Note that, the protective layer 13 covers the entire outer surface 107 of the substrate 10 except for the diffusion resistance layer 14 and the rear end 102 side of the substrate 10.

At least the diffusion resistance layer 14 and the electrode extraction portion 122 are not covered by the protective layer 13 and are exposed.

The A/F sensor element 1 of the present embodiment is used by inserting the distal end 101 side into an exhaust gas pipe or an exhaust manifold (refer to FIG. 1-FIG. 4).

In the A/F sensor element 1, the outer surface 107 of the distal end 101 side is exposed to the measured gas (exhaust gas).

On the other hand, the inner surface 106 is exposed to a reference gas (air).

In the A/F sensor element 1, the electrolyte part 103, and the reference gas side electrode 11 and the measured gas side electrode 12 formed respectively on opposing surfaces of the electrolyte part 103 form the electrochemical cell, and when each of the electrodes 11, 12 is exposed to the reference gas and the measured gas, respectively, limiting current is generated between the electrodes 11, 12 by a difference in oxygen concentration of these gases, and an air-fuel ratio can be detected form a value of the limiting current.

Hereinafter, a method of manufacturing the A/F sensor element 1 of the present embodiment will be described.

In the present embodiment, the A/F sensor element 1 is manufactured by performing a first molding step, a second molding step, a degreasing step, a firing step, and an electrode molding step.

Figure 6:
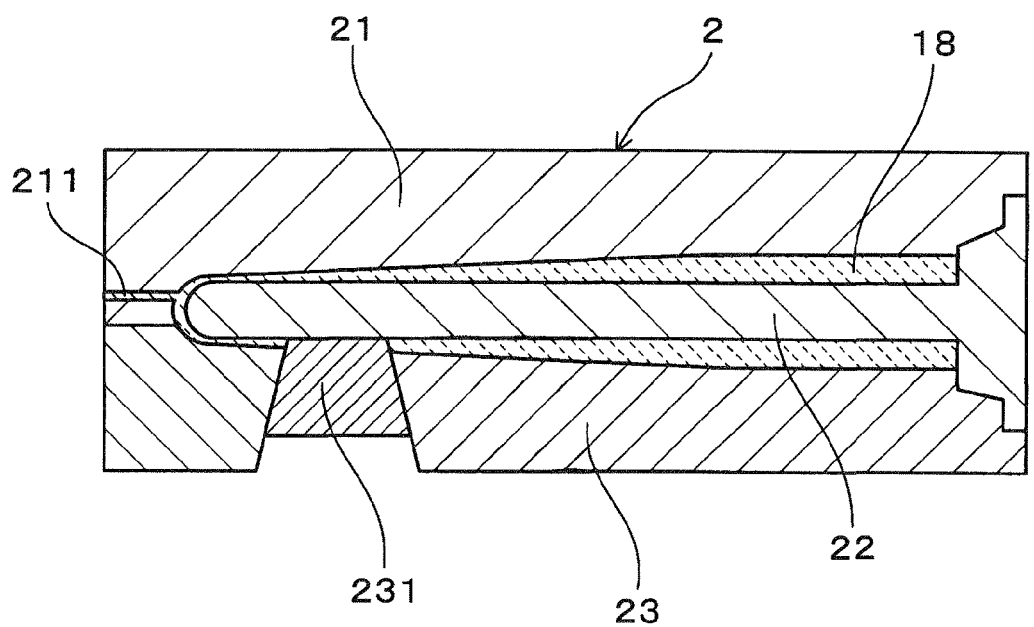
FIG. 6 is an explanatory view showing a sectional structure of the mold in a state where the cavity is filled with clay for forming a substrate in the first embodiment.
Figure 7:
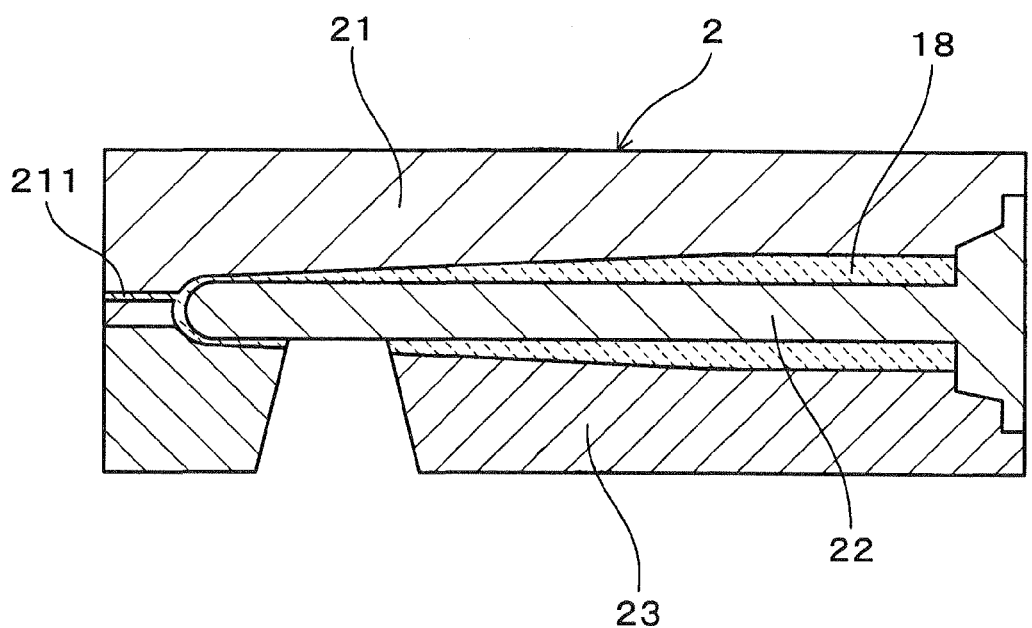
FIG. 7 is an explanatory view showing a sectional structure of the mold in a state where the movable mold for closing is removed in the first embodiment.
Figure 8:
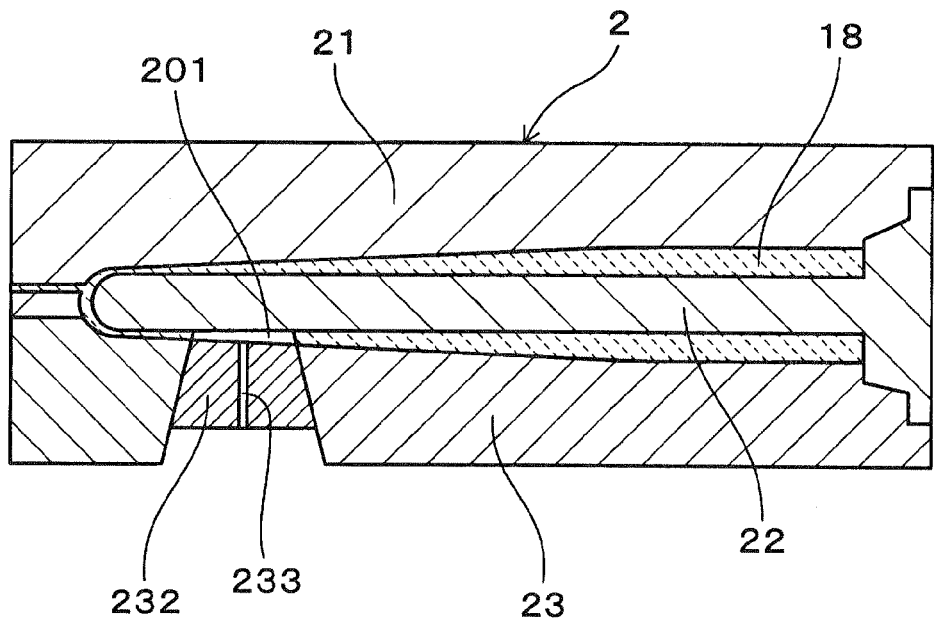
FIG. 8 is an explanatory view showing a sectional structure of the mold form with the cavity for forming the electrolyte part by placing the movable mold for forming the electrolyte part in first embodiment.

In the first molding step, substrate-forming clay 18 containing the insulating ceramic material is molded to the shape of the substrate 10 (a bottomed cylindrical shape) to which a space 201 is formed in a position where the electrolyte part is formed (refer to FIG. 6-FIG. 8).

In the second molding step, electrolyte-forming clay 19 containing a solid electrolyte material is molded by being filled in the space 201 mentioned above (refer to FIG. 8 and FIG. 9).

In the degreasing step, a molded body 100 (refer to FIG. 10) obtained after the first molding step and the second molding step is degreased.

In the firing step, the molded body 100 is fired.

Further, in the electrode molding step, the electrode portions 11, 12, the electrode lead portion 121, and the electrode extraction portion 122 are formed on the substrate 10 obtained after firing (refer to FIG. 1-FIG. 3).

Hereinafter, the method for manufacturing the A/F sensor element 1 of the present embodiment will be explained in detail.

First, substrate-forming clay is obtained by blending alumina powder, paraffin resins, styrene-butadiene copolymer resin, and stearic acid, and mixing after adding pure water to the blend and heating it.

Figure 5:
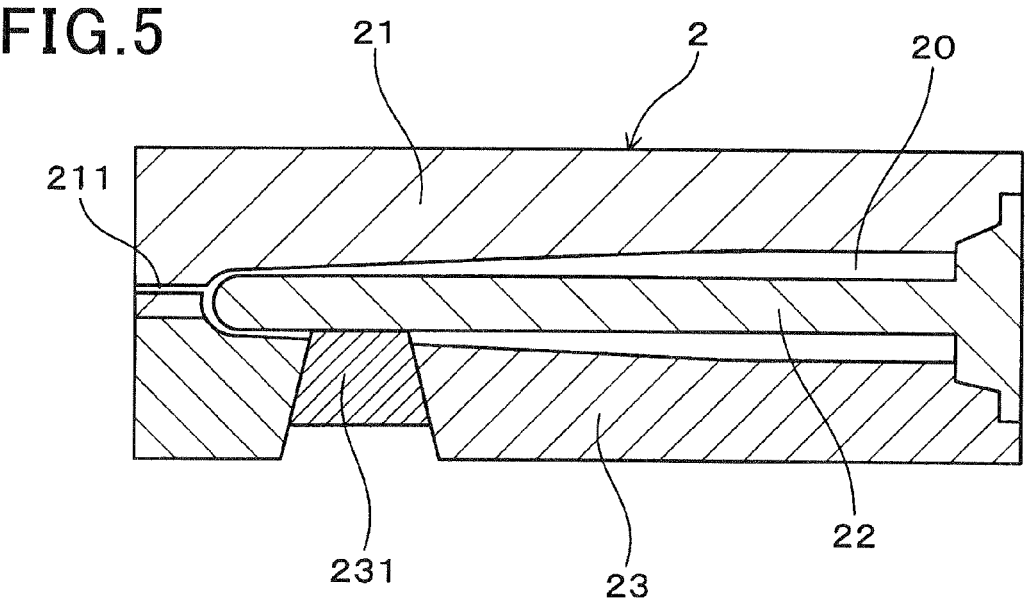
FIG. 5 is an explanatory view showing a sectional structure of a mold where a part of a cavity is closed by a movable mold in the first embodiment.

Then, as shown in FIG. 5, a mold 2 (metal mold) to which a cavity 20 of the shape of the substrate (a bottomed cylindrical shape) is formed is prepared.

As shown in FIG. 5, in the present embodiment, the mold 2 is composed of three major components, namely, an upper mold 21, a center mold 22, and a lower mold 23. The upper mold 21, the center mold 22, and the lower mold 23 are separable from one another.

A clay inlet 211 for feeding the material into the cavity 20 formed by the upper mold 21, the center mold 22, and the lower mold 23 is formed in the upper mold 21.

Further, a movable mold 231 that closes a portion of the cavity 20 is provided in the lower mold 23.

The movable mold 231 is provided so as to close a forming position of the electrolyte part 103 in the cavity 20 (refer to FIG. 2).

Next, as shown in FIGS. 5 and 6, the substrate-forming clay 18 is filled into the cavity 20 of the mold 2 through the clay inlet 211 to perform an injection molding (first molding step).

The injection molding is performed in a condition where the forming position of the electrolyte in the cavity 20 of the mold 2 is closed by the movable mold 231.

Next, electrolyte-forming clay is obtained by blending zirconia powder, yttria powder, paraffin resins, styrene-butadiene copolymer resin, and stearic acid, and mixing after adding pure water to the blend and heating it.

Figure 9:
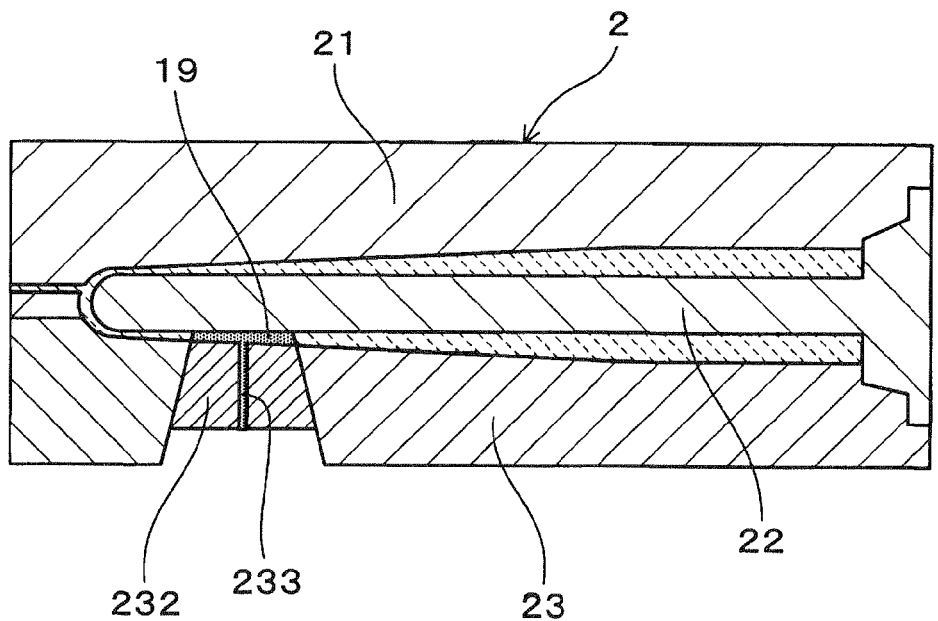
FIG. 9 is an explanatory view showing a sectional structure of the mold in a state where the cavity is filled with clay for forming an electrolyte in the first embodiment.

Then, as shown in FIG. 7-FIG. 9, the electrolyte-forming clay 19 is filled into the space 201 formed by opening the forming position of the electrolyte part closed by the movable mold 231 to perform the injection molding.

Specifically, as shown in FIG. 7, the movable mold 231 that closes the formation position of the electrolyte part is removed after injection molding of the substrate-forming clay 18 (refer to FIG. 6), then, as shown in FIG. 8, replaced by another movable mold 232 where another cavity (space 201) is formed in the forming position of the electrolyte part.

Another clay inlet 233 for feeding the material into the space 201 is formed in the movable mold 232.

Then, as shown in FIG. 9, the electrolyte-forming clay 19 is filled into the space 201 through the clay inlet 233 provided in the movable mold 232 to perform the injection molding (second molding step).

Figure 10:
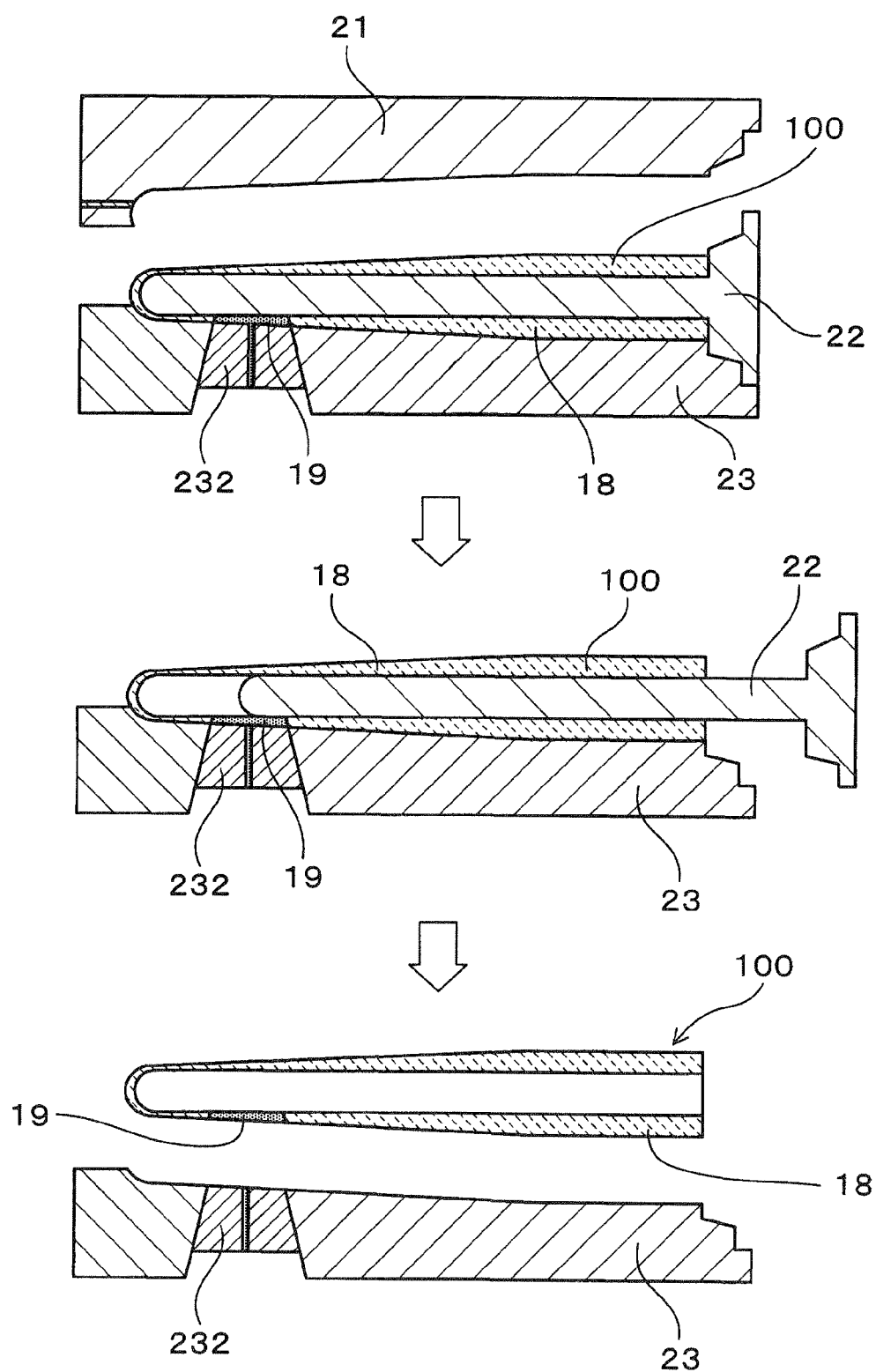
FIG. 10 shows an explanatory view showing a manner of removing a molded body from the mold in cross section in the first embodiment.

Next, as shown in FIG. 10, the upper mold 21, the center mold 22, and the lower mold 23 are removed sequentially from the molded body 100 after the injection molding, and the molded body 100 having the bottomed cylindrical shape is obtained.

A part of the side wall of the molded body 100 is made of the electrolyte-forming clay 19, and the rest is made of the substrate-forming clay 18.

Next, after degreasing the molded body 100 (degreasing step), the molded body 100 is fired (firing step).

Thereby, as shown in FIG. 4, the substrate 10 made of the insulating ceramic having the bottomed cylindrical shape in which the electrolyte part 103 made of the solid electrolyte is embedded in the part of the side wall 104 is obtained.

Then, as shown in FIG. 1-FIG. 3, platinum is deposited on the inner surface 106 and the outer surface 107 of the substrate 10 by electroless plating, and by heat-treating the substrate 10 at the temperature of 1000 degrees C., the reference gas side electrode 11 and the measured gas side electrode 12 are formed (electrode molding step).

In the present embodiment, the reference gas side electrode 11 is formed over the entire inner surface 106 of the substrate 10, and the measured gas side electrode 12 is formed in the same size as the electrolyte part 103.

Further, the electrode leads 121 that extend toward the rear end 102 side of the substrate 10 from the measured gas side electrode 12 and the ring-shaped electrode extraction portion 122 that surrounds the outer periphery of the substrate 10 formed in the rear end 102 side of the substrate 10 are formed on the outer surface 107 of the substrate (refer to FIGS. 1-3).

The electrode lead portion 121 and the electrode extraction portion 122 are also formed using platinum by electroless plating similarly to the reference gas side electrode 11 and the measured gas side electrode 12.

Then, the porous diffusion resistance layer 14 made of $MgO.Al_2O_3$ spinel is formed so as to completely cover at least the measured gas side electrode 12. The diffusion resistance layer 14 is formed by plasma spraying.

Further, the protective layer 13 made of the dense body of $MgO.Al_2O_3$ spinel is formed on the outer surface of the substrate 10 by plasma spraying except for the diffusion resistance layer 14 and the rear end 102 of the substrate 10.

In the manner described above, as shown in FIG. 1-FIG. 3, the A/F sensor element 1 having the substrate 10 made of the insulating ceramic with the bottomed cylindrical shape, the electrolyte part 103 made of the solid electrolyte, and the pair of electrodes 11, 12 is obtained.

In the A/F sensor element 1 of the present embodiment, as shown in FIG. 2-FIG. 4, the electrolyte part 103 made of the solid electrolyte is embedded in at least the portion of the side wall 104 of the substrate 10 made of the insulating ceramic to constitute the part of the side wall 104.

Therefore, it becomes possible to reduce the amount of the solid electrolyte to be used. As a result, even if an expensive rare earth such as yttria is added to the partially stabilized zirconia, for example, the amount to be used can be reduced.

Therefore, the A/F sensor element 1 can be manufactured at low cost.

Further, by constituting the part of the side wall 104 with the electrolyte part 103, it becomes possible to reduce the size of the A/F sensor element 1.

Thereby, it becomes possible to quickly heat the A/F sensor element 1, thus the quick activation is improved.

Further, as shown in FIG. 1-FIG. 3, the A/F sensor element 1 of the present embodiment is used by inserting a rod-like heater 3 in the substrate 10 that has the bottomed cylindrical shape.

The contact position 109 to the heater 3 within the substrate 10 is constituted by the insulating ceramic having the higher thermal conductivity than the solid electrolyte.

That is, the electrolyte part 103 made of the solid electrolyte having a low thermal conductivity is not present in the substrate 10 at the contact position 109 to the heater 3, but the insulating ceramic with the high thermal conductivity is present.

Therefore, heat from the heater 3 is transmitted immediately to the substrate 10 made of the insulating ceramic having the high thermal conductivity.

Therefore, it becomes possible that the time required for heating is shortened, thus the A/F sensor element 1 can be activated quicker.

Further, the part of the side wall 104 of the substrate 10 is made of the electrolyte part 103, and the distal end 101 side and the rear end 102 side from the electrolyte part 103 of the side wall 104 is formed by the insulating ceramic.

Therefore, in the A/F sensor element 1 of the present embodiment, the heater 3i s inserted into the substrate 10 having the bottomed cylindrical shape, and an end 31 of the heater 3 is in contact with the bottom surface of the substrate 10.

Thus, it becomes possible to easily achieve the above configuration that the contact position 109 of the substrate 10 to the heater 3 is the insulating ceramics with high thermal conductivity.

Further, in the present embodiment, a level difference at boundary section 105 between the substrate 10 and the electrolyte part 103 of the inner surface 106 side and the outer surface 107 side of the substrate 10 is measured by a laser displacement gauge.

The measurement is performed by a non-contact measurement manner. As a result, the level difference is about 3 µm at the most. Thus, in the A/F sensor element 1 of the present embodiment, the level difference at the boundary section 105 between the substrate 10 and the electrode 103 is very small.

Therefore, it becomes possible to suppress the occurrence of the stress concentration on the level difference at the boundary section 105 between the substrate 10 and the electrode 103 during thermal shock such as firing the substrate 10 or the A/F sensor element 1 being covered by water.

As a result, it becomes possible to prevent cracks from occurring in the A/F sensor element 1.

Moreover, the A/F sensor element 1 has the bottomed-cylindrical-shaped substrate 10.

Therefore, it becomes possible to avoid formation of corners or level differences where thermal stress is easily concentrated when covered by water, like a plate-like A/F sensor element, for example.

Therefore, it becomes possible to further avoid the occurrence of cracks due to the stress concentration.

Further, it becomes possible to avoid the formation of the corners as described above, it becomes possible to prevent the element from damaging by the collision of the corners when assembled to another member. Therefore, assembling to other members becomes easy.

Furthermore, in the A/F sensor element 1 of the present embodiment, the boundary between the side wall 104 and the bottom portion 108 of the substrate 10 has the curved surface.

Therefore, it becomes possible to prevent the heat stress from concentrating in the boundary section between the side wall 104 and the bottom portion 108. Therefore, it becomes possible to prevent cracks from occurring even more reliably.

In the present embodiment, alumina is a main component of the insulating ceramic of the substrate 10. Therefore, it becomes possible to improve the electrical insulation and thermal conductivity of the substrate 10.

Further, partially stabilized zirconia is a main component of the solid electrolyte of the electrolyte part 103. Therefore, the A/F sensor element 1 is able to produce excellent sensitivity.

Furthermore, the A/F sensor element 1 of the present embodiment has the diffusion resistance layer 14 made of the porous ceramic that covers at least the measured gas side electrode 12.

Therefore, it is possible to suppress the diffusion of gas on to the surface of the measured gas side electrode 12, thus the detection accuracy of the sensor is increased.

In the first molding step, substrate-forming clay 18 is molded to the shape of the substrate 10 to which the space 201 is formed in the position where the electrolyte part is formed, and in the second molding step, electrolyte-forming clay 19 is molded by being filled in the space 201 (refer to FIG. 5-FIG. 10).

Thereby, the substrate-forming clay 18 and the electrolyte-forming clay 19 can be molded integrally into the bottomed cylindrical shape (refer to FIG. 10).

As a result, by performing the firing step, the substrate 10 of the bottomed cylindrical shape having the electrolyte part 13 made of a solid electrolyte embedded in at least the part of the side wall 104 can be obtained.

In the second molding step, the electrolyte-forming clay 19 is filled into the space 201 formed in advance in the first molding step, and is integrally formed as described above.

Therefore, as described above, it becomes possible to almost eliminate the level difference at the boundary section 105 between the substrate 10 and the electrode 103 after firing.

In the first molding step and the second molding step of the present embodiment, the electrolyte-forming clay 18 and the substrate-forming clay 19 are molded by injection using the metal mold 2 (refer to FIGS. 5-10).

In particular, the substrate-forming clay 18 is molded by injection into the cavity 20 of the mold 2 in the state where the forming position of the electrolyte part in the cavity 20 of the mold 2 is closed by the movable mold 231 in the first molding step, and the electrolyte-forming clay 19 is molded by injection into the space 201 formed by opening the forming position of the electrolyte part closed by the movable mold 231 in the second molding step.

Therefore, the A/F sensor element 1 with almost no level difference at the boundary section 105 between the substrate 10 and the electrode 103 described above can be easily manufactured (refer to FIG. 1-FIG. 3).

First Comparative Embodiment

The present comparative embodiment is an example of an A/F sensor element in which a whole substrate having the bottomed cylindrical shape is formed with the solid electrolyte.

Specifically, an oxygen concentration sensor as such an A/F sensor element is disclosed in FIG. 3 of the Japanese Patent Application Laid-Open Publication No. 53-139595, for example.

Even when a substrate is formed in the same size as in the first embodiment, the A/F sensor element with the entire substrate constituted by the solid electrolyte (partially stabilized zirconia) requires 20 times more of the expensive zirconia in the comparative embodiment than that of the first embodiment.

Further, since the entire substrate is made of the solid electrolyte having a low thermal conductivity, even heated by the heater, it takes four times longer for a typical comparative embodiment to reach a measurable predetermined temperature as the sensor as compared with the first embodiment.

Second Comparative Embodiment

The present comparative embodiment is an example of an A/F sensor element in which a solid electrolyte layer having a pair of electrodes on front and back surfaces thereof is wrapped around a rod-like core made of alumina.

Specifically, an oxygen sensor as such an A/F sensor element is disclosed in a first embodiment (FIG. 1-FIG. 3) of the Japanese Patent Application Laid-Open Publication No. 61-272649, for example.

The A/F sensor element of the present comparative embodiment, a step of wrapping a green sheet that becomes the solid electrolyte layer around the core is needed during the production thereof.

Therefore, a certain degree of strength is required for the core and the green sheet, thus it is necessary to increase the thickness of the green sheet.

As a result, size of the solid electrolyte layer having low thermal conductivity increases, and it becomes less likely to be heated by the heater.

In contrast, in the A/F sensor element of first embodiment described above, since the solid electrolyte part 103 is embedded in the part of the side wall 104, the size of the element 1 may be reduced (refer to FIG. 1-FIG. 4).

Further, in the A/F sensor element 1 of the first embodiment, the contact position 105 to the heater 3 in the substrate 10 is made of the insulating ceramic having a high thermal conductivity (refer to FIG. 1-FIG. 3).

Therefore, compared with an element having the structure of the second comparative embodiment, the A/F sensor element 1 of the first embodiment can be activated quickly.

Actually, the A/F sensor element having the structure of the second comparative embodiment requires the time two times longer to reach the measurable predetermined temperature as the sensor as compared with the first embodiment.

(Modifications)

Although the electrolyte part made of the solid electrolyte is formed in at least the part of the side wall of the bottomed cylindrical shaped substrate made of the insulating ceramic in the first embodiment mentioned above, the electrolyte part can also be formed in a plurality of parts of the side wall of the substrate.

Examples of a substrate in which formation pattern of the electrolyte part of the substrate and a shape of the substrate are changed from those of the first embodiment are explained in the following modifications.

FIGS. 11-19 of which the following modifications 1-3 refer show a shape of the substrate and a formation position of the electrolyte part on the substrate, and the configuration of other components of the A/F sensor element such as the electrode portion, the porous protective layer, or the heater are omitted.

However, in the sectional views of FIG. 12, FIG. 15 and FIG. 18, the heater that is inserted in the substrate is indicated by a dotted line for convenience of explaining the positional relationship between the substrate and the heater which is described later.

(First Modification)

The present modification is an example of a substrate where a pair of electrolyte parts opposing to each other is formed in a distal end side of a side wall.

Figure 11:
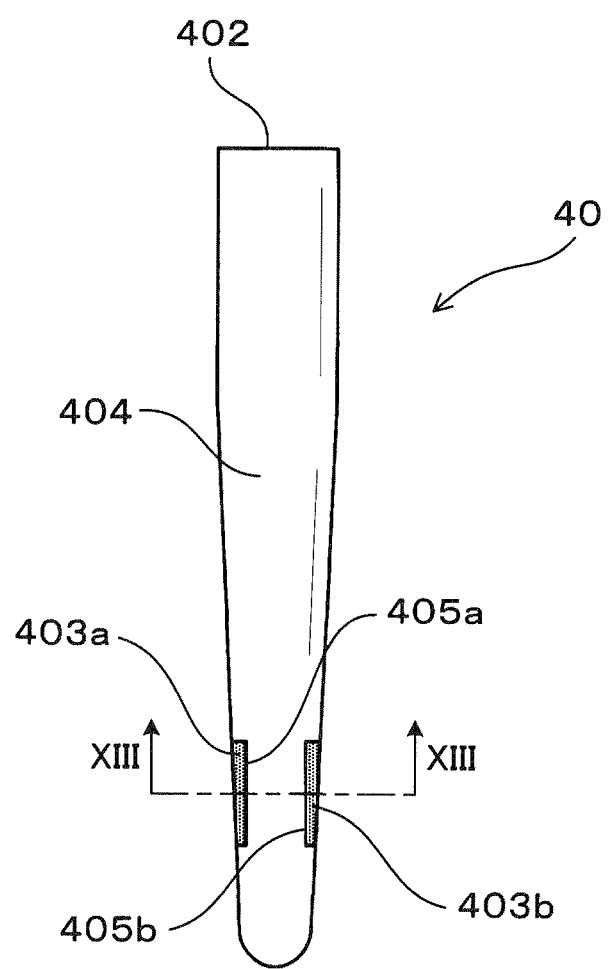
FIG. 11 shows a side view of a substrate formed with a pair of electrolyte parts opposing a side wall in a first modification.
Figure 12:
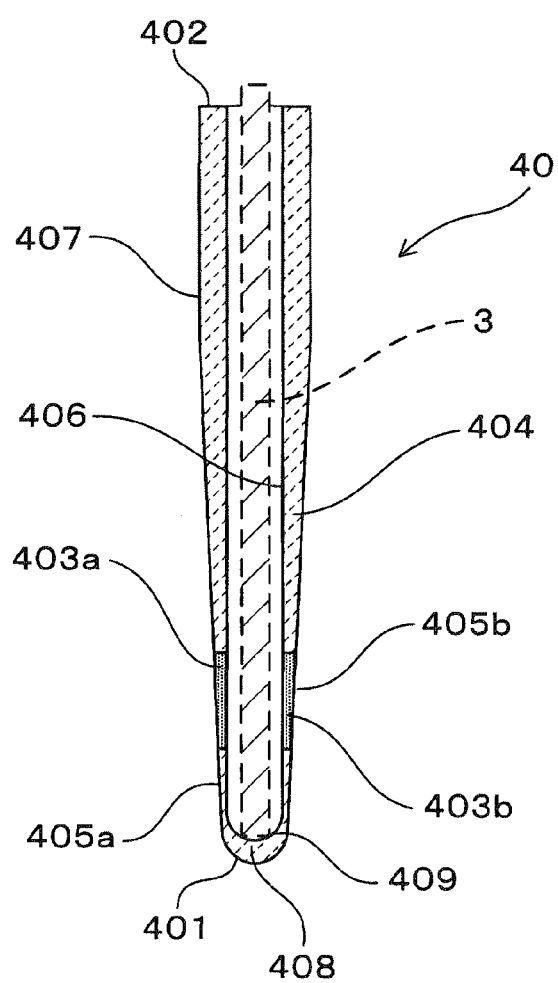
FIG. 12 shows a sectional view of the substrate in a direction parallel to a plane in FIG. 11.
Figure 13:
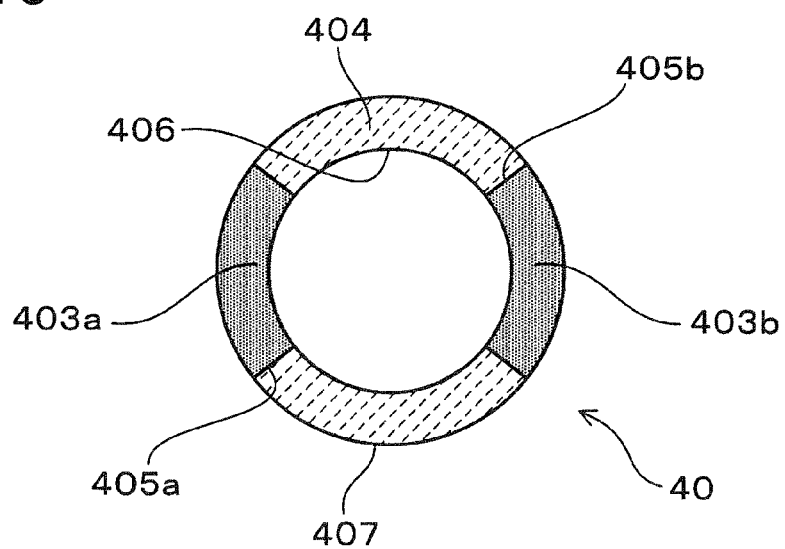
FIG. 13 shows a sectional view taken along a line XIII-XIII in FIG. 11.

As shown in FIGS. 11-13, a substrate 40 in the present modification has a bottomed cylindrical shape, and has a pair of electrolyte parts 403a, 403b in positions opposite to each other in a side wall 404.

The electrolyte parts 403a, 403b are formed near a distal end 401 of the side wall 404, and are embedded in the side wall 404 to form parts of the side wall 404.

The parts of the side wall 404 of the substrate 40 are formed by the electrolyte parts 403a, 403b made of the solid electrolyte, and an entire remaining surface in the distal end 401 side and a rear end 402 side from the electrolyte parts 403a, 403b is formed by the insulating ceramic.

Accordingly, in the same manner as in the first embodiment, the electrode portions (not shown) are also formed on the inner surface 406 and the outer surface 407 of the substrate 40 of the present modification, and the A/F sensor element is prepared by forming the protective layer (not shown) on the outer surface 407.

When the heater 3 (shown by dotted lines in FIG. 12) is inserted and disposed into the substrate 40 up to a bottom portion 408, for example, the contact position 409 to the heater 3 within the substrate 40 is constituted by the insulating ceramic (refer to FIG. 12).

(Second Modification)

The present modification is an example of a substrate where a cylindrical electrolyte part is formed around an entire circumference of a distal end side of a side wall.

Figure 14:
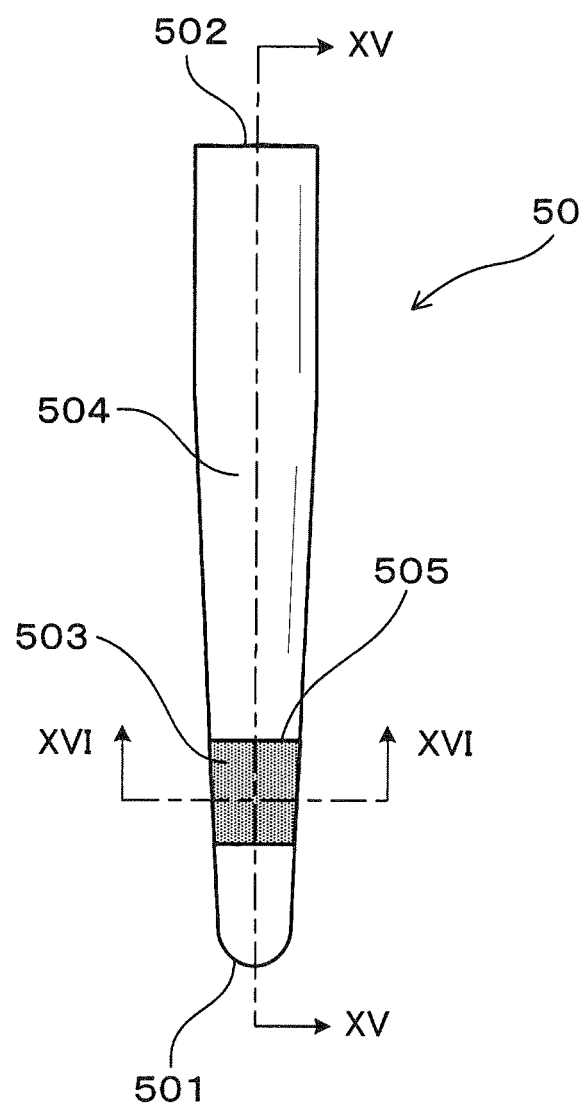
FIG. 14 shows a side view of a substrate formed with an electrolyte part on entire periphery of a side wall in a second modification.
Figure 15:
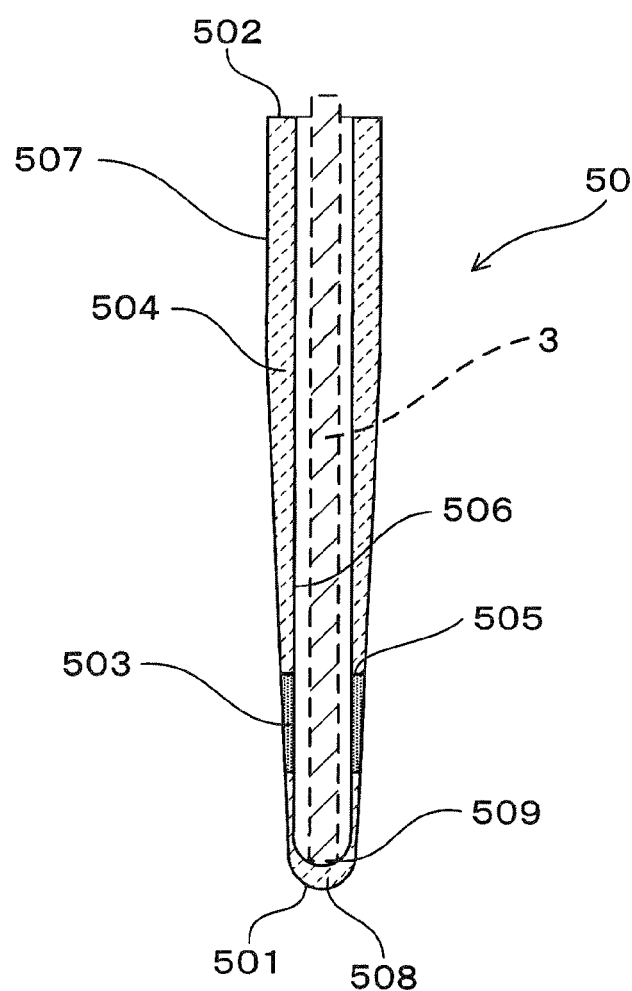
FIG. 15 shows a sectional view taken along a line XV-XV in FIG. 14.
Figure 16:
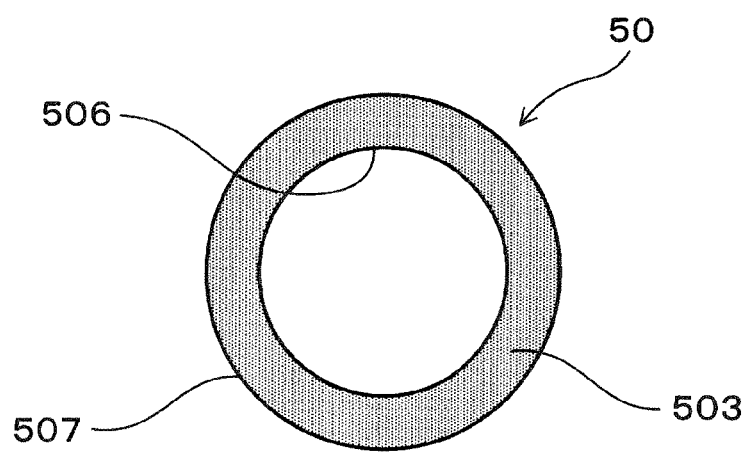
FIG. 16 shows a sectional view taken along a line XVI-XVI in FIG. 14.

As shown in FIGS. 14-16, a substrate 50 in the present modification has a bottomed cylindrical shape, and has a cylindrical electrolyte part 503 formed around an entire circumference of a distal end 501 side of a side wall 504.

The electrolyte part 503 is embedded in the side wall 504 to form a part of the side wall 504.

The part of the side wall 504 of the substrate 50 is formed by the electrolyte part 503 made of the solid electrolyte, and an entire remaining surface in the distal end 501 side and a rear end 502 side from the electrolyte part 503 is formed by the insulating ceramic.

Accordingly, in the same manner as in the first embodiment, the electrode portions (not shown) are also formed on the inner surface 506 and the outer surface 507 of the substrate 50 of the present modification, and the A/F sensor element is prepared by forming the protective layer (not shown) on the outer surface 507.

When the heater 3 (shown by dotted lines in FIG. 15) is inserted and disposed into the substrate 450 up to a bottom portion 508, for example, the contact position 509 to the heater 3 within the substrate 50 is constituted by the insulating ceramic (refer to FIG. 15).

(Third Modification)

The present modification is an example of a substrate where a boundary between a side wall and a bottom portion is not formed in a curved surface, but the bottom portion is formed at a right angle relative to the side wall.

Figure 17:
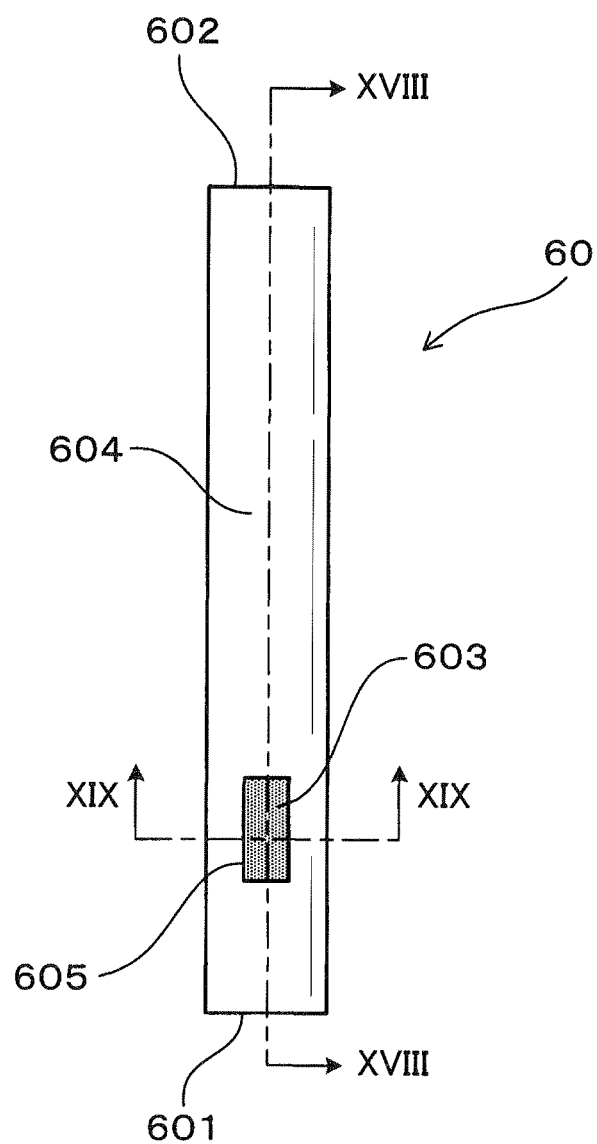
FIG. 17 shows a side view of a substrate in which an electrolyte part is embedded in a part of a side wall, having a flat bottom surface perpendicular to the side wall in a third modification.
Figure 18:
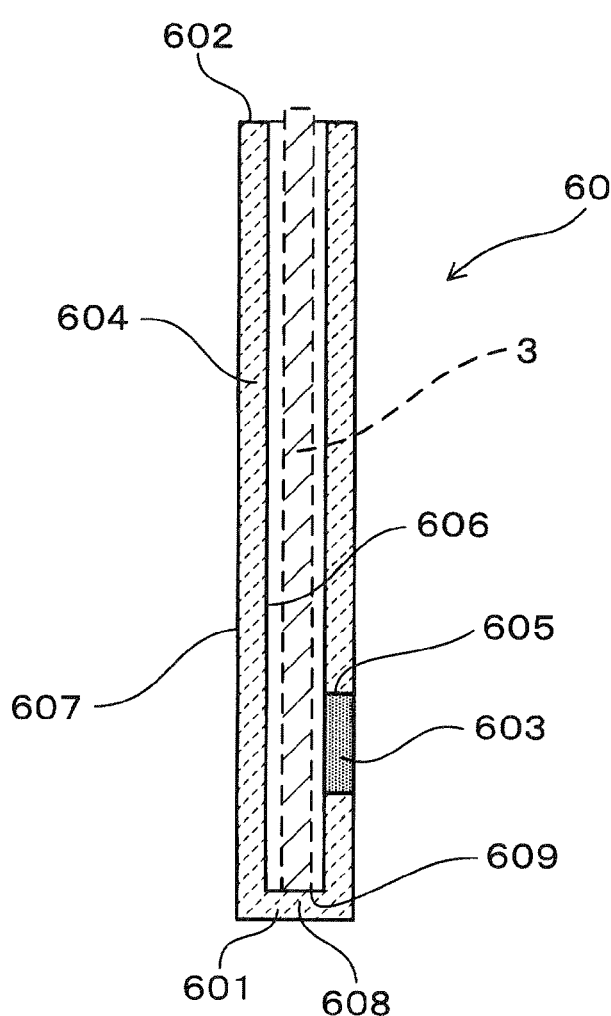
FIG. 18 shows a sectional view taken along a line XVIII-XVIII in FIG. 17.
Figure 19:
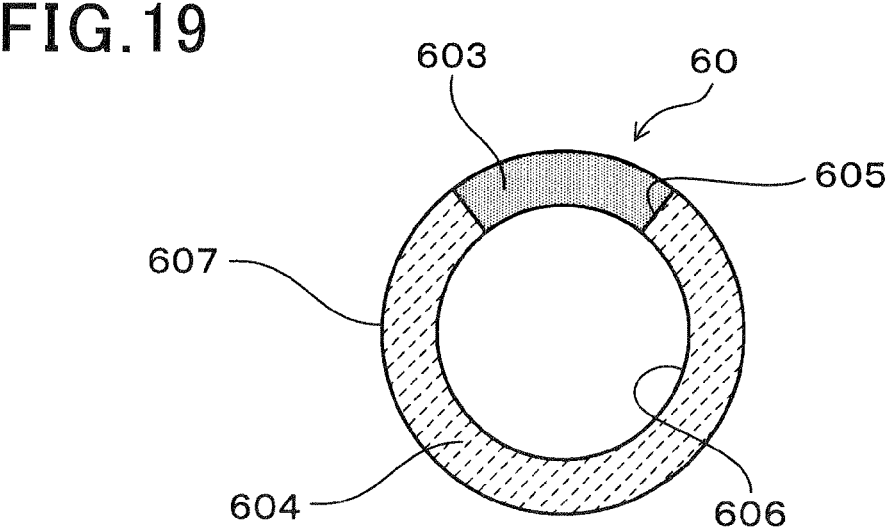
FIG. 19 shows a sectional view taken along a line XIX-XIX in FIG. 17.

As shown in FIGS. 17-19, a substrate 60 in the present modification has a bottomed cylindrical shape, and like the first embodiment, has an electrolyte part 603 formed in a distal end 601 side of a side wall 604.

The side wall 604 has a cylindrical shape, and a bottom portion 608 is provided in a direction perpendicular to the side wall 604. An angle between the side wall 604 and the bottom portion 608 is a right angle.

The substrate 60 of the present modification is formed by the electrolyte part 603 made of the solid electrolyte, and an entire remaining surface in the distal end 601 side and a rear end 602 side from the electrolyte part 603 is formed by the insulating ceramic.

Accordingly, in the same manner as in the first embodiment, the electrode portions (not shown) are also formed on the inner surface 606 and the outer surface 607 of the substrate 60 of the present modification, and the A/F sensor element is prepared by forming the protective layer (not shown) on the outer surface 607.

When the heater 3 (shown by dotted lines in FIG. 18) is inserted and disposed into the substrate 650 up to a bottom portion 608, for example, the contact position 609 to the heater 3 within the substrate 60 is constituted by the insulating ceramic (refer to FIG. 18).

The substrates 40, 50 in the first and second modifications described above may be manufactured by the same manner as in the first embodiment, i.e., performing the first molding step, the second molding step, and the firing step except that the shape of the space where the electrolyte-forming clay is filled to be changed according to the shape of the electrolyte part 403a, 403b, 503 (refer to FIG. 11-FIG. 16).

Further, the substrate 60 of the third modification may be manufactured by the same manner as in the first embodiment, i.e., performing the first molding step, the second molding step, and the firing step with the exception of using a mold having a cavity that is formed such that the bottom portion 608 is formed at the right angle relative to the side wall 604 (refer to FIG. 17-FIG. 19).

Therefore, it becomes possible to substantially eliminate any level difference in the boundary section 405a, 405b, 505, 605 between the substrate 40, 50, 60 made of the insulating ceramic and the electrolyte part 403a, 403b, 503, 603 even in the substrate 40, 50, 60 of each modification like the first embodiment.

Further, when forming a A/F sensor element using the substrate 40, 50, 60 of the first to third modifications, the electrode sections may be formed appropriately depending on the formation position and shape the electrolyte part 403a, 403b, 503, 603 so that the electrochemical cell is constructed.

The diffusion resistance layer and the protective layer may be formed on the outer surface of the substrate 40, 50, 60 so as to at least cover the electrode portion (measured gas side electrode) formed on the electrolyte part 403a, 403b, 503, 603.

By forming the electrode portion, the diffusion resistance layer, and the protective layer, it becomes possible to configure the A/F sensor element in the same manner as in the first embodiment even in each modification, and the A/F sensor element in each modification performs the same functions and effects as in the first embodiment.

It should be appreciated that, in the modifications, components identical with or similar to those in the first embodiment are given the same reference numerals, and structures and features thereof will not be described in order to avoid redundant explanation.

What is claimed is:

1. A method of manufacturing an air-fuel (A/F) sensor, the air-fuel (A/F) sensor comprising:
a substrate made of an insulating ceramic having a bottomed cylindrical shape with a closed distal end and an opened rear end;
an electrolyte part made of a solid electrolyte; and
a pair of electrodes;
wherein, the insulating ceramics is made of a material having a higher thermal conductivity than the solid electrolyte;
the electrolyte part is embedded in at least a portion of the side wall of the substrate to constitute a part of the sidewall;
the pair of the electrode portion is formed on an inner surface and an outer surface of the side wall, respectively, and is formed at positions sandwiching the electrolyte part;
the air-fuel (A/F) sensor element is used by inserting a rod-like heater in the substrate having the bottomed cylindrical shape; and
the substrate is formed of the insulating ceramic at a contact position to the heater within the substrate,
the method comprising:
a first molding step for molding substrate-forming clay containing the insulating ceramic material to the shape of the substrate to which a space is formed in a position where the electrolyte part is formed;
a second molding step for molding electrolyte-forming clay containing a solid electrolyte material by being filled in the space;
a firing step for manufacturing the substrate having the electrolyte part by firing; and
an electrode molding step for forming the electrode portion.

2. The method of manufacturing the air-fuel (A/F) sensor element according to claim 1,
wherein, the electrolyte-forming clay and the substrate-forming clay are molded by injection using a metal mold in the first molding step and the second molding step.

3. The method of manufacturing the air-fuel (A/F) sensor element according to claim 2,
the substrate-forming clay is molded by injection into a cavity of the mold in a state where a forming position of the electrolyte part in the cavity of the mold is closed by a movable mold in the first molding step, and the electrolyte-forming clay is molded by injection into the space formed by opening the forming position of the electrolyte part closed by the movable mold in the second molding step.

* * * * *